United States Patent [19]

Helphrey

[11] Patent Number: 4,596,462

[45] Date of Patent: Jun. 24, 1986

[54] SPECTROPHOTOMETER PURGE APPARATUS

[75] Inventor: David B. Helphrey, Santa Ana, Calif.

[73] Assignee: Beckman Instruments, Inc., Fullerton, Calif.

[21] Appl. No.: 472,421

[22] Filed: Mar. 4, 1983

[51] Int. Cl.$^4$ ................................................. G01J 3/02
[52] U.S. Cl. .................................. 356/300; 220/22.1; 356/319; 356/244
[58] Field of Search .................. 356/300, 319-325, 356/244, 51, 346; 220/22, 22.1, 22.3, 22.4, 22.5, 22.6

[56] References Cited

U.S. PATENT DOCUMENTS

| | | | |
|---|---|---|---|
| 2,020,373 | 11/1935 | Petzold, Jr. | 220/22.3 |
| 3,899,252 | 8/1975 | Dimeff | 356/51 |
| 4,081,100 | 3/1978 | Presby | 220/22.1 X |
| 4,322,165 | 3/1982 | Ellebracht et al. | 356/316 |
| 4,436,215 | 3/1984 | Kleinert et al. | 220/22.2 X |

OTHER PUBLICATIONS

Helms et al., *Spectrochimica Acta.*, vol. 19, 1963, pp. 819-828.

"Beam Condenser for IR-4200", Beckman Instructions 015-555357, Oct. 1976.

*Primary Examiner*—F. L. Evans
*Attorney, Agent, or Firm*—W. H. May; P. R. Harder; S. R. Markl

[57] ABSTRACT

Spectrophotometer purge apparatus comprising a sample compartment including a plurality of walls defining a first sample purge volume. The apparatus may further include a volume reducing wall and fastening means for removably fixing the volume reducing wall within the sample compartment to thereby define a second sample purge volume smaller than the first sample purge volume. A purge gas inlet introduces purge gas into the sample purge volumes. Further the apparatus may comprise a movable partition forming one of the plurality of walls and the volume reducing wall. In such an embodiment, the fastening means may further include means for removably fixing the movable partition to thereby define the first sample purge volume. The apparatus advantageously enables the sample purge volume to be adjusted as required to thereby optimize purge efficiency in a spectrophotometer.

6 Claims, 2 Drawing Figures

SPECTROPHOTOMETER PURGE APPARATUS

FIELD OF THE INVENTION

The present invention relates generally to the field of spectroscopy and, more particularly, to sample compartment purge apparatus. The invention is particularly suited for use in applications requiring various sample compartment volumes.

DESCRIPTION OF THE PRIOR ART

In the field of spectroscopy, it is well known that substances external to the sample under analysis may influence the spectral analysis of the sample. For example, water vapor in the atmosphere surrounding the sample may absorb radiation over a wavelength range important to the analysis of the sample, thereby influencing the accuracy of the spectral data obtained.

To overcome such difficulty, prior spectrophotometer instruments have included a purge system which can be controlled to supply pressurized purge gas into a sample compartment. The purge gas is selected such that it will not interfere with the desired spectral analysis. In use, the sample is placed into the sample compartment and the sample compartment is closed. The purge system is then activated to flood or purge the sample compartment with purge gas. The time required to purge the sample compartment, that is, purge time, is related to the volume of the sample compartment and the flow rate of the purge gas into the sample compartment.

It is often necessary to open the sample compartment frequently to change or adjust the sample. Each time the sample compartment is opened, interfering substances may be introduced into the sample compartment. Consequently, the sample compartment must be purged each time it is opened, thus delaying the analysis of the sample and decreasing the overall efficiency and usefulness of the spectrophotometer.

In prior instruments, attempts have been made to minimize purge time and thus increase purge efficiency and instrument usefulness by providing a small volume sample compartment in such instruments. However, it is also desirable to permit analytical accessories to be fitted into the sample compartment and such accessories often require a large sample compartment volume. In order to accommodate analytical accessories, such instruments have been fitted with sample compartment extensions to enlarge the sample compartment volume. However, such compartment extensions are generally awkward to use with spectrophotometers and increase the cost and complexity of accessories.

SUMMARY OF THE INVENTION

A spectrophotometer purge apparatus in accordance with the present invention overcomes the limitations and drawbacks described above. The spectrophotometer purge apparatus is easily adapted to provide a large sample compartment for accepting various spectroscopic accessories. Moreover, when a large sample compartment volume is not required, the spectrophotometer purge apparatus of the present invention enables the purge volume to be easily decreased, thereby improving purge efficiency and spectrophotometer usefulness.

Toward the foregoing ends, a spectrophotometer purge apparatus in accordance with the present invention comprises a sample compartment including a plurality of walls defining a first sample purge volume. A purge gas inlet introduces a purge gas into the sample purge volume. Advantageously, the apparatus further includes a volume reducing wall and fastening means for removably fixing the volume reducing wall within the sample compartment to thereby uniquely define a second smaller sample purge volume and thus increase the purge efficiency.

Further, the apparatus may include a movable partition which forms one of the plurality of sample compartment walls and the volume reducing wall. The movable partition may be fixed by the fastening means with respect to selected ones of the walls to thus define the first sample purge volume.

DESCRIPTION OF THE PREFERRED EMBODIMENTS

Figure 1:
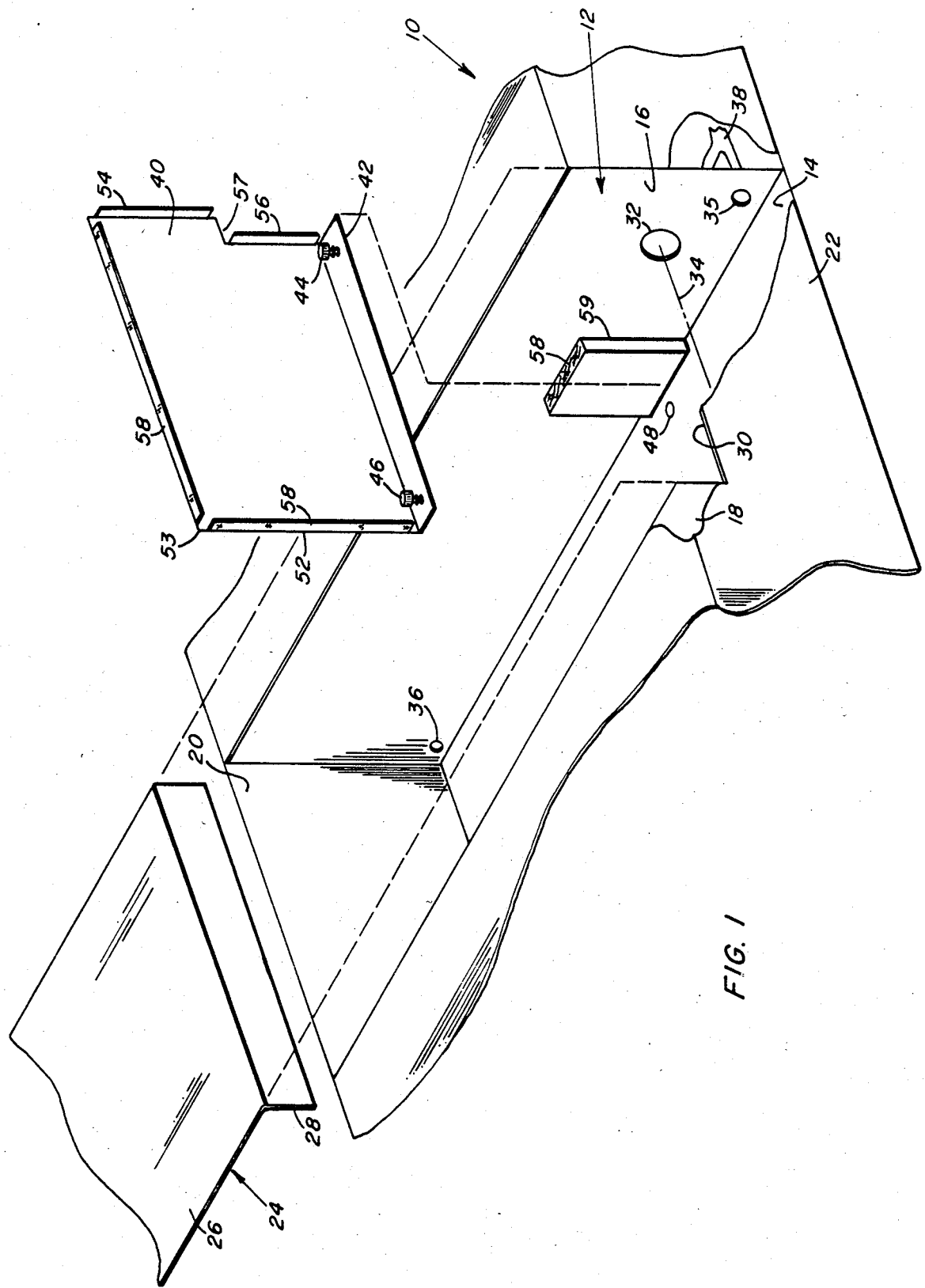
FIG. 1 is a perspective view of a spectrophotometer purge apparatus in accordance with one embodiment of the present invention. The apparatus is shown in a partially exploded format with its cover and partition members removed to better illustrate the structure of the apparatus.

With reference to FIG. 1, a spectrophotometer purge apparatus in accordance with a first embodiment of the present invention may be part of a spectrophotometer 10. The spectrophotometer 10 includes a sample compartment designated generally as 12. The sample compartment 12 is formed by a plurality of walls including a floor 14, opposite vertical side walls 16 and 18, a back wall 20, a front wall 22, and a cover 24. The cover 24 is removable such that samples and accessories may be easily placed into the sample compartment 12. The cover 24 includes a top 26 adapted to cover and substantially seal the upper edges of the side walls 16 and 18 and the back wall 20, and a lip 28 adapted to cover and substantially seal a corresponding cutout 30 in the front wall 22.

Within the sample compartment 12, an opening 32 is formed through the side wall 16 near the front wall 22. The opening 32, along with a corresponding opposite opening in the side wall 18 (not shown), enables radiation to follow a path 34 through the sample compartment 12. A sample may be placed into the path 34 for spectroscopic analysis. Alternatively, an accessory fitted into the sample compartment 12 may interrupt the path 34 to thereby insert additional optical elements into the path 34 in a well known conventional fashion. The opening 32 and the opposite opening are preferably covered with a material invisible to the radiation so as to contain purge gas in the sample compartment 12.

A first purge gas inlet 35 is formed through the side wall 16 near the front wall 22 and a second similar purge gas inlet 36 is also formed through the side wall 16 near the back wall 20. The purge gas inlets 35 and 36 are connected by a suitable conduit 38 to a source of purge gas and a valve or other suitable means (not shown) well known to those skilled in the art for controlling the flow of purge gas through the inlets 35 and 36 into the sample compartment 12.

Further in accordance with the present invention, the spectrophotometer purge apparatus includes a volume reducing wall or partition 40 which is adapted to fit within the sample compartment 12. The partition 40 includes a bottom flange 42 which is adapted to seat against the floor 14. The bottom flange 42 carries two fasteners such as captured thumb screws 44 and 46. The thumb screw 44 is adapted to engage a threaded opening 48 formed into the floor 14 and the thumb screw 46 is likewise adapted to engage a similar threaded opening (not shown) in the floor 14. The partition further includes a plurality of edge flanges 52–56. A sealing material 58, such as expanded foam is carried by the flanges 52–56 and the bottom flange 42. The partition 40 includes a notch 57 adapted to fit around a rectangular protrusion 59 formed against the side wall 16 within the sample compartment 12. Foam 58 may also be applied to the upper surface of the protrusion 59. With the partition 40 fixed within the sample compartment 12 by means of the thumb screws 44 and 46, the foam 58 forms a seal between the partition 40 and the floor 14, side walls 16 and 18, the cover 24, and the protrusion 59.

In use, the partition 40 may be removed from the sample compartment 12. In such a configuration, the sample compartment 12 provides a large volume for receiving, for example, spectroscopic accessories or large samples. With a sample in place, the cover 24 is positioned to close the sample compartment 12 and purge gas is admitted through the purge inlets 35 and 36 into the purge compartment 12. The gas previously in the sample compartment 12 may flow out of the sample compartment 12, for example, around the outer edges of the cover 24. The purge time is related to the overall purge volume, defined by the cover 24, side, back and front walls 14–24, floor 14, and protrusion 59, and the flow rate of purge gas through the purge inlets 35 and 36. Because two inlets 35 and 36 are used in the embodiment illustrated, each inlet 35 and 36 may be considered as purging a portion of the total purge volume of the sample compartment.

When a small sample is to be analyzed, or a sample with a small accessory is to be used, the partition 40 is fixed within the sample compartment 12 by means of the thumb screws 42 and 46. With the cover 24 in place, a sample purge volume, which is advantageously smaller than the volume previously purged by the inlet 35, is defined by the side walls 16 and 18, floor 14, cover 24, front wall 22, protrusion 59, and the partition 40. Purge time is decreased and purge efficiency is uniquely increased, thereby increasing the efficiency and usefulness of the spectrophotometer 10. Moreover, unlike prior instruments, no extension is required to the sample compartment 12 to accommodate the volume required by most accessories.

Figure 2:
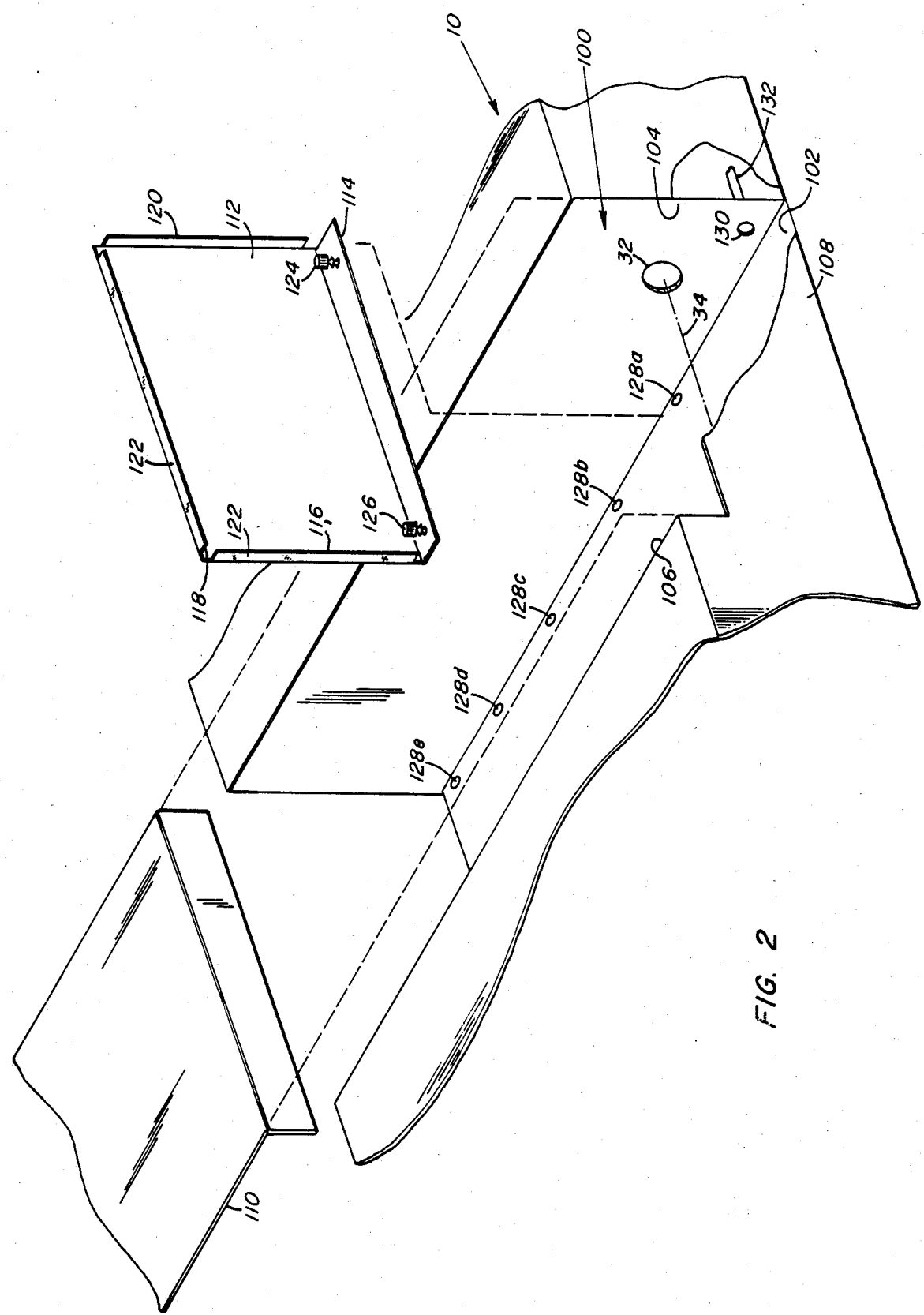
FIG. 2 is a perspective view (similar to FIG. 1) of a spectrophotometer purge apparatus in accordance with another embodiment of the present invention.

An alternative embodiment of the present invention is shown with reference to FIG. 2. The spectrophotometer 10 has a sample compartment 100 which is formed by a plurality of walls including a floor 102, opposite vertical side walls 104 and 106, a front wall 108, a cover 110, and a partition 112. The partition 112 includes a plurality of flanges 114–120 that carry a sealing material 122. The bottom flange 114 also carries captured thumb screws 124 and 126. The thumb screw 124 is adapted to engage a plurality of threaded openings 128a–128e formed into the floor 102. The thumb screw 126 is adapted to engage a similar plurality of threaded openings (not shown) in the floor 102 near the side wall 106. Unlike the embodiment of FIG. 1 which includes both a back wall 20 and a separate volume reducing wall or partition 40 to define different sample purge volumes, the embodiment of FIG. 2 employs a single partition 112 which may be repositioned to define various sample purge volumes. The apparatus shown in FIG. 2 includes an opening 32 and an opposite opening (not shown) as described with reference to FIG. 1 and a purge gas inlet 130 connected via a conduit 132 to suitable means for controlling the flow of purge gas into the sample compartment 100.

In using the spectrophotometer purge apparatus as shown in FIG. 2, the partition 112 is fixed within the sample compartment 100 by engaging the thumb screw 124 with one of the openings 128a–e and engaging the thumb screw 126 with one of the corresponding holes near the side wall 106. The position of the partition 112 within the sample compartment 100 may be advantageously determined to minimize the sample purge volume purged by the flow of purge gas through the purge inlet 130. For example, the partition 112 may be fixed in a position over the opening 128a and one of the corresponding openings near the side wall 106 when a small sample is placed into the sample compartment. However, if an analytical accessory is to be placed into the sample compartment 100 requiring a larger sample compartment volume, the position of the partition 112 may be adjusted so as to secure the partition over one of the remaining openings 128b–e and one of the corresponding openings near the side wall 106.

In both of the embodiments disclosed herein, a user may easily and uniquely vary the sample purge volume contained within the sample compartment to thus optimize purge efficiency for a wide range of sample and analytical accessory sizes. Both embodiments enable a large sample or accessory to be placed into the sample compartment. However, the sample purge volume can be quickly reduced to thus improve purge efficiency when sample or accessory size permits, thereby increasing the efficiency and usefulness of the spectrophotometer 10.

Having disclosed two embodiments of the present invention, further alternatives, variations and equivalents will be apparent to those skilled in the art which fall within the spirit and scope of the appended claims. As examples which are not intended to limit a range of equivalents, the embodiment of FIG. 2 may include a back wall similar to the back wall of FIG. 1 and the embodiment of FIG. 1 may be adapted to enable the partition 40 to be secured at a plurality of positions between the plane defined by the dotted line 60 and the front wall 108.

What is claimed is:

1. A spectrophotometer having a purge apparatus comprising:
    a sample compartment comprising a plurality of walls defining a first sample purge volume;
    said compartment having a removable cover substantially sealing said plurality of walls,
    a volume reducing wall;
    fastening means for removably fixing the volume reducing wall within the sample compartment with respect to selected ones of the plurality of walls to thereby define a covered sample compartment having a second sample purge volume smaller than the first sample purge volume; and
    purge gas inlet means for introducing purge gas into the sample purge volumes.

2. A spectrophotometer as in claim 1, wherein the sample compartment includes a movable partition, the movable partition forming one of the plurality of walls of the sample compartment and the volume reducing wall.

3. A spectrophotometer as in claim 1, wherein said fastening means includes means for fastening the volume reducing wall at a plurality of positions within the sample compartment to thereby define a plurality of second sample purge volumes.

4. A spectrophotometer as in claim 2, wherein the movable partition carries a sealing material along its perimeter to form a seal between said partition, the plurality of walls, and the cover thereby defining a sealed sample purge volume.

5. A spectrophotometer purge apparatus comprising:
 a sample compartment comprising a plurality of walls defining a sealed sample purge volume;
 fastening means for removably fixing at least one of the walls with respect to the other walls, the at least one wall thereby varying the sealed purge volume defined by the wall; and
 purge gas inlet means for introducing purge gas into the sealed sample purge volume.

6. A spectrophotometer purge apparatus comprising:
 a sample purge volum defined by a covered and sealed sample compartment, said sample compartment having a plurality of walls;
 means for adjusting the sample purge volume by repositioning at least one wall of said sample compartment, thereby adjusting the size of the sample compartment.

* * * * *

UNITED STATES PATENT AND TRADEMARK OFFICE
CERTIFICATE OF CORRECTION

PATENT NO. : 4,596,462

DATED : June 24, 1986

INVENTOR(S) : David B. Helphrey

It is certified that error appears in the above-identified patent and that said Letters Patent is hereby corrected as shown below:

Column 6, line 3      after the word "sealed", insert the word --sample--

Signed and Sealed this

Ninth Day of December, 1986

*Attest:*

DONALD J. QUIGG

*Attesting Officer*      *Commissioner of Patents and Trademarks*